United States Patent
Gupta et al.

(10) Patent No.: US 10,184,909 B2
(45) Date of Patent: Jan. 22, 2019

(54) CONNECTION AND CORROSION DETECTION

(71) Applicant: Apple Inc., Cupertino, CA (US)

(72) Inventors: Vishal Gupta, Sunnyvale, CA (US); Timothy M. Johnson, San Jose, CA (US); Nilay D. Jani, San Jose, CA (US); Yehonatan Perez, Menlo Park, CA (US)

(73) Assignee: Apple Inc., Cupertino, CA (US)

( * ) Notice: Subject to any disclaimer, the term of this patent is extended or adjusted under 35 U.S.C. 154(b) by 40 days.

(21) Appl. No.: 15/275,202

(22) Filed: Sep. 23, 2016

(65) Prior Publication Data

US 2018/0088067 A1    Mar. 29, 2018

(51) Int. Cl.
*G01R 27/26* (2006.01)
*G01N 27/02* (2006.01)
*G01R 31/04* (2006.01)
*H01R 43/00* (2006.01)

(52) U.S. Cl.
CPC ......... *G01N 27/028* (2013.01); *G01R 31/045* (2013.01); *H01R 43/002* (2013.01); *H01R 2201/20* (2013.01)

(58) Field of Classification Search
USPC .................... 324/538–543, 756.05
See application file for complete search history.

(56) References Cited

U.S. PATENT DOCUMENTS

| | | | | |
|---|---|---|---|---|
| 4,232,262 A | * | 11/1980 | Emo ............... | G01R 31/043 324/538 |
| 5,097,213 A | * | 3/1992 | Hunting ........... | G01R 31/043 324/519 |
| 5,440,263 A | * | 8/1995 | Fournel ............ | G01R 19/16519 327/143 |
| 2015/0208154 A1 | * | 7/2015 | Turner .............. | H04R 29/00 381/58 |
| 2017/0358922 A1 | * | 12/2017 | Bacon .............. | H02H 9/04 |

* cited by examiner

*Primary Examiner* — Vincent Q Nguyen
(74) *Attorney, Agent, or Firm* — Kilpatrick Townsend & Stockton, LLP

(57) ABSTRACT

Methods, structures, and apparatus that are able to detect the presence of a connection to a device contact of an electronic device and are also able to detect the presence of contamination at the device contact. A host device includes a connection detection circuit and a contamination detection circuit connected to the device contact. The connection detection circuit includes a pull-up resistor that is pulled down by a pull-down resistor in an accessory device following a connection. The contamination detection circuit includes a current source to provide a current at the device contact and measurement circuitry to measure a resulting voltage.

21 Claims, 12 Drawing Sheets

CONNECTION AND CORROSION DETECTION

BACKGROUND

The amount of data transferred between electronic devices has grown tremendously the last several years. Large amounts of audio, streaming video, text, and other types of data content are now regularly transferred among desktop and portable computers, media devices, handheld media devices, displays, storage devices, and other types of electronic devices.

Power and data may be provided from one electronic device to another over cables that may include one or more wire conductors, fiber optic cables, or other conductors. Connector inserts may be located at each end of these cables and may be inserted into connector receptacles in the communicating or power transferring electronic devices. Contacts in or on a connector insert may form electrical connections with corresponding contacts in a connector receptacle. Other devices may have contacts at a surface of a device. Pathways for power and data may be formed when devices are attached together or positioned next to each other and corresponding contacts are electrically connected to each other.

Once these pathways are formed, the connected devices may share power, data, or both. Accordingly, it may be desirable for a device to be able to detect when such a connection has been made.

These various contacts in connector inserts, in connector receptacles, or on a surface of a device, may be exposed to the local environment. These contacts may encounter liquid, moisture, or other damaging contaminants. For example, liquids may be spilled on these contacts or a device may be set down such that its contacts land in a puddle of liquid. Users may swim or exercise while wearing or holding an electric device. These activities may put contacts for the electronic devices in a position to encounter various contaminants.

These liquids or other contaminants may corrode and damage the contacts. This corrosion may be greatly exacerbated by the presence of an electric field, such as when a voltage is applied to a contact. Accordingly, it may be desirable for a device to be able to detect the presence of a contaminant at a contact so that the possible damage may be mitigated.

Thus, what is needed are methods, structures, and apparatus that are able to detect the presence of a connection to a contact of an electronic device and are also able to detect the presence of contamination at the contact.

SUMMARY

Accordingly, embodiments of the present invention may provide methods, structures, and apparatus that may be able to detect the presence of a connection to a contact of an electronic device and may also be able to detect the presence of contamination at the contact.

An illustrative embodiment of the present invention may provide connection detect circuitry that may detect a connection of an accessory to a host device. The connect detect circuitry may include a pull-up resistor coupled to a device power contact and to an input of a window comparator. An accessory may include a pull-down resistor coupled to an accessory power contact. When the host device and accessory are connected, the device power contact and the accessory power contact may be electrically connected. The pull-down resistor coupled to the accessory power pin may draw current through the pull-up resistor coupled to a device power contact, thereby lowering the voltage of the device power contact. This lowered voltage may be detected by the window comparator. The window comparator may then provide a signal indicating that a connection between the host device and the accessory has been formed.

It may be undesirable to maintain a connection between the pull-up resistor in the host device and the pull-down resistor in the accessory after a connection has been detected. For example, it may create a current path that may waste power. It may also lower the voltage seen at the power contacts. This current path may also make it difficult to detect the presence of contamination at the device power contact. Accordingly, embodiments of the present invention may provide an active pull-down. The active pull-down may provide a pull-down resistance for a first duration following a reception of a power supply at an accessory power contact and a high impedance or open circuit thereafter.

In these and other embodiments of the present invention, the active pull-down may include a resistor in series with a transistor. A capacitor divider including a first capacitor and a second capacitor may be coupled between the accessory power contact and ground. The middle node of the capacitor divider may be coupled to a gate of the transistor. A current limiting resistor may be coupled between the middle node of the capacitor divider and the gate of the transistor. A Zener diode having a cathode coupled to the gate of the transistor and an anode coupled to a source of the transistor may work with the current limiting resistor to protect the transistor from rapid applications of a voltage at the accessory power contact. A bleed resistor may be connected from middle node of the capacitor divider to ground to set the length of the first duration.

Once the active pull-down disconnects, it may cause the voltage on the accessory power contact to increase, thereby once again activating the active pull-down. To prevent this, the pull-up resistor in the host device may be disconnected, for example by opening a switch in series with the resistor. The removal of this resistor may also facilitate the detection of contamination by removing a stray current path.

Once the active pull-down has disconnected from the accessory power contact, the host device may attempt to detect the presence of contamination at a device power contact. An illustrative embodiment of the present invention may provide a current detect circuit that may detect the presence of contamination at a device power contact. A current may be provided to the device power contact and the resulting voltage may be measured. A contamination that lowers the impedance at the device power contact may cause the measured voltage to be low. The low measured voltage may indicate that a contamination is present.

In these and other embodiments of the present invention a calibration loop may be provided. A current may be provided to a known calibration resistor. The resulting voltage may be measured and used to calibrate the contamination detect circuitry.

In these and other embodiments of the present invention, current may be selectively applied to the calibration resistor during a calibration routine and to the device power contact during a detection of contamination. A measurement system may include an analog-to-digital converter and may be selectively coupled to the calibration resistor during a calibration routine and the device power contact during a detection of contamination.

In these and other embodiments of the present invention, a current provided to a contaminant having a high impedance may result in a high voltage beyond a range of the measurement circuit of the contamination detect circuitry. Accordingly, a switch may be coupled between the calibration resistor and the device power contact. Adding the calibration resistor in parallel with the impedance of the contamination may reduce the resulting voltage to where it may be in the measurement range of the measurement system of the contamination detect circuitry.

In these and other embodiments of the present invention, stray impedances in the host device and accessory may be accounted for in order to more accurately determine the impedance of a contamination at a device power contact. For example, during contamination detection, a current may be provided to the device power contact. This current may see the impedances of the host device, the accessory, and the contamination in parallel. The host device impedance may be determined during manufacturing or at another time and stored in the host device. The accessory impedance may be provided by the accessory manufacturer and read from the accessory by the host device after a connection has been detected. For example, the accessory impedance may be read from a register on the accessory, while the host device impedance may be read from a register on the host device. Values for either or both of these impedances over temperature and voltage supply may be stored in these registers.

When a current is applied to for a long period of time, some fairly innocuous contaminants, such as deionized (DI) water may have a similar impedance as more harmful contaminants, such as sweat or pool water. This convergence of impedances may not occur when current is applied for a shorter period of time. Accordingly, in these and other embodiments of the present invention, a current provided to the calibration resistor or the device power contact may be a pulsed current. For example, multiple current pulses having a known duration and amplitude relationship may be applied. These relative short current pulses may also reduce the damage caused by the contaminant that is being detected, as compared to a longer, sustained current.

In these examples, a connection detect circuit and contamination detect circuit may be located on a host device, while an active pull-down may be located on an accessory. In these and other embodiments of the present invention, a connection detect circuit and contamination detect circuit may be located on an accessory, while an active pull-down may be located on a host device.

Also, in these examples, the connection detect circuit and the contamination detect circuit may be connected to the same contact. In these and other embodiments of the present invention, the connection detect circuit and the contamination detect circuit may be connected to separate and different contacts. Also, in these examples, the connection detect circuit and the contamination detect circuit may be connected to a power contact.

In these and other embodiments of the present invention, the connection detect circuit and the contamination detect circuit may be connected to a contact other than a power contact. For example, either or both the connection detect circuit and the contamination detect circuit may be connected to another type of contact such as a contact used for an enable signal, low-frequency data signal, or other data, control, bias, supply, or other type of contact.

Embodiments of the present invention may provide contacts for connector receptacles and connector inserts that may be located in, and may connect to, various types of devices, such as portable computing devices, tablet computers, desktop computers, laptops, all-in-one computers, wearable computing devices, cell phones, smart phones, media phones, storage devices, portable media players, navigation systems, monitors, power supplies, video delivery systems, adapters, remote control devices, chargers, and other devices. These contacts may provide pathways for power and signals that are compliant with various standards such as one of the Universal Serial Bus (USB) standards including USB Type-C, High-Definition Multimedia Interface® (HDMI), Digital Visual Interface (DVI), Ethernet, DisplayPort, Thunderbolt™, Lightning™, Joint Test Action Group (JTAG), test-access-port (TAP), Directed Automated Random Testing (DART), universal asynchronous receiver/transmitters (UARTs), clock signals, power signals, and other types of standard, non-standard, and proprietary interfaces and combinations thereof that have been developed, are being developed, or will be developed in the future. Other embodiments of the present invention may provide contacts that may be used to provide a reduced set of functions for one or more of these standards. In various embodiments of the present invention, these contacts may be used to convey power, ground, signals, test points, and other voltage, current, data, or other information.

Various embodiments of the present invention may incorporate one or more of these and the other features described herein. A better understanding of the nature and advantages of the present invention may be gained by reference to the following detailed description and the accompanying drawings.

DESCRIPTION OF ILLUSTRATIVE EMBODIMENTS

Figure 1:
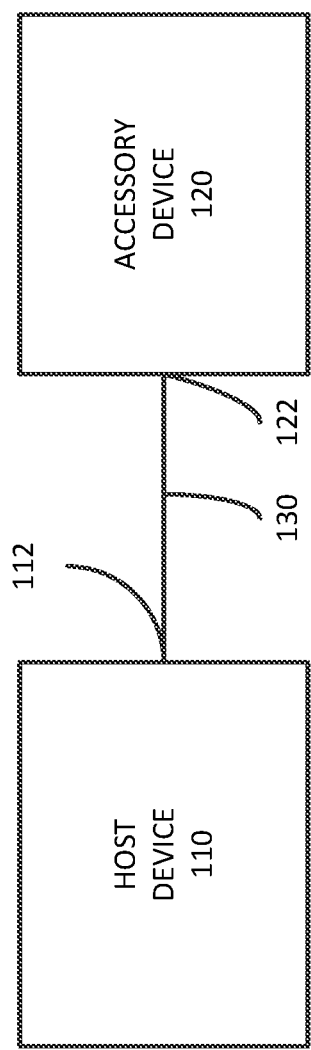
FIG. 1 illustrates an electronic system that may be improved by the incorporation of an embodiment of the present invention.

FIG. 1 illustrates an electronic system that may be improved by the incorporation of an embodiment of the present invention. This figure, as with the other included figures, is shown for illustrative purposes and does not limit either the possible embodiments of the present invention or the claims.

In this example, host device 110 may be connected to accessory device 120 in order to share data, power, or both. Specifically, contacts 112 on host device 110 may be electrically connected to contacts 122 on accessory device 120. Contacts 112 on host device 110 may be electrically connected to contacts 122 on accessory device 120 via cable 130. In other embodiments of the present invention, contacts 112 on host device 110 may be directly and electrically connected to contacts 122 on accessory device 120. In various embodiments of the present invention, contacts 112 and 122 may be power contacts or other types of contacts. Examples of embodiments of the present invention where contacts 112 and 122 are power contacts are shown in the following figures.

Figure 2:
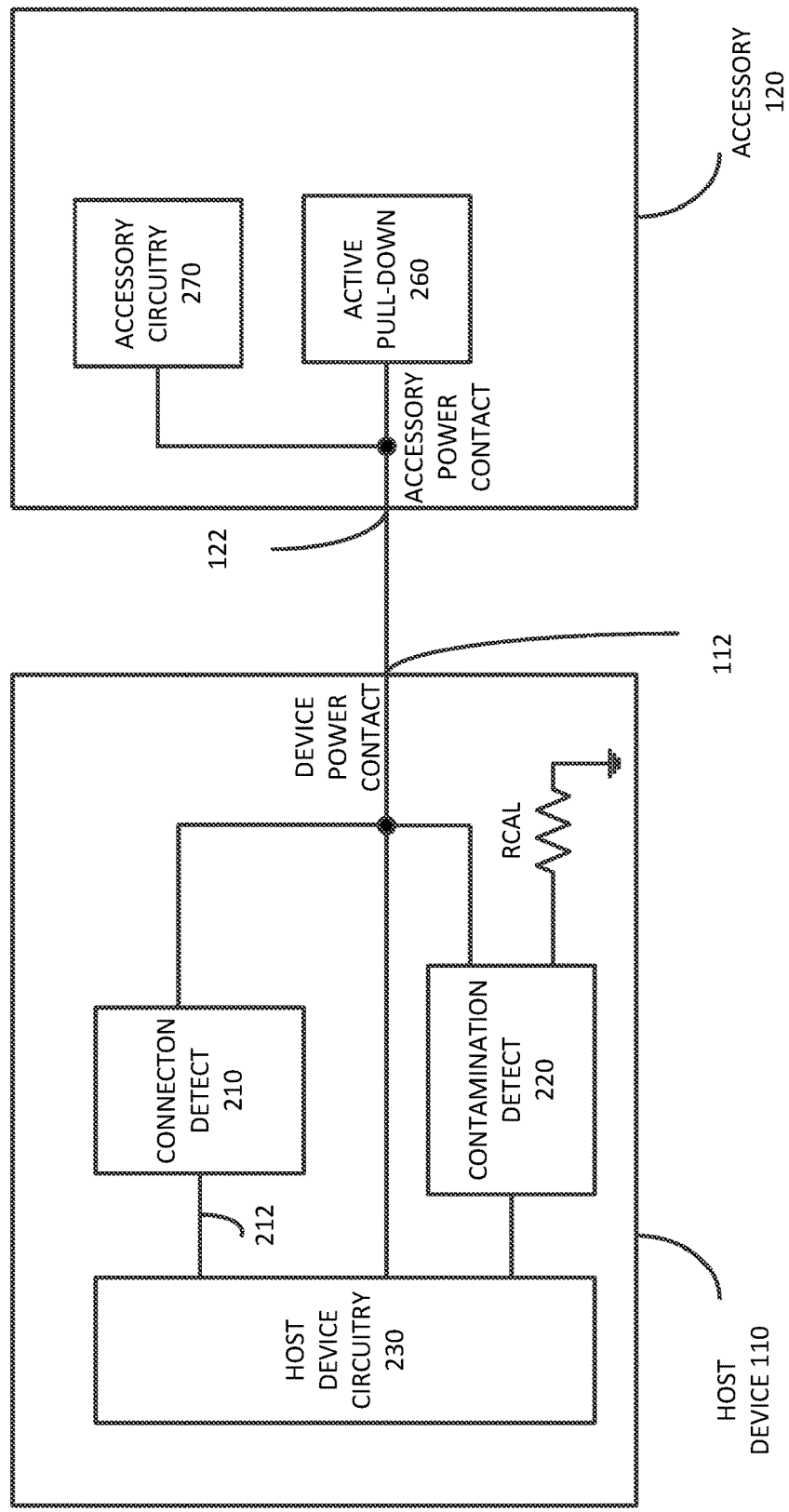
FIG. 2 illustrates an electronic system according to an embodiment of the present invention.

FIG. 2 illustrates an electronic system according to an embodiment of the present invention. This figure includes host device 110 and accessory 120. Host device 110 may include device power contact 112 which may electrically connect to accessory power contact 122. Device power contact 112 of host device 110 may be directly and physically connected to accessory power contact 122, or device power contact 112 may be connected to accessory power contact 122 through a cable (not shown).

It may be desirable for host device 110 to be able to determine when accessory 120 is connected. It may also be desirable to determine whether a possibly caustic or corrosive contaminant is present at device power contact 112. Accordingly, host device 110 may include connection detect circuit 210 and contamination detect circuit 220. Connection detect circuit 210 may be coupled between host device circuitry 230 and device power contact 112. Contamination detect circuit 220 may be coupled between host device circuitry 230 and device power contact 112. Contamination detect circuit 220 may be further coupled to a calibration resistor RCAL.

Connection detect circuit 210 of host device 110 may include a pull-up resistor that works in conjunction with a pull-down resistor connected to accessory power contact 122 in accessory 120. But the presence of a pull-down resistor connected to accessory power contact 122 in accessory 120 may complicate the detection of contaminations at device power contact 112 of host device 110. Accordingly, accessory 120 may include active pull-down 260. Active pull-down 260 may provide a pull-down resistance for a first duration following the reception of power on accessory power contact 122. Following the first duration, the active pull-down circuit 260 may provide a high impedance or open circuit. In these and other embodiments of the present invention, a connection may be detected by connection detect circuit 210 in approximately 5 milliseconds, between 2-10 milliseconds, in 3-8 milliseconds, or it may be detected after a different duration having another approximate value in another range. In these and other embodiments of the present invention, an active pull-down may be disconnected after a first duration of 50 milliseconds, between 20-100 milliseconds, in 30-80 milliseconds, or it may have a different approximate value in another range.

In these examples, connection detect circuit 210 and contamination detect circuit 220 may be located on host device 110, while active pull-down 260 may be located on accessory 120. In these and other embodiments of the present invention, connection detect circuit 210 and contamination detect circuit 220 may be located on accessory 120, while active pull-down 260 may be located on a host device 110.

Also, in these examples, connection detect circuit 210 and contamination detect circuit 220 may be connected to the same contact. In these and other embodiments of the present invention, connection detect circuit 210 and contamination detect circuit 220 may be connected to separate and different contacts. Also, in these examples, connection detect circuit 210 and contamination detect circuit 220 may be connected to a power contact. In these and other embodiments of the present invention, connection detect circuit 210 and contamination detect circuit 220 may be connected to a contact other than a power contact.

In these and other embodiments of the present invention, the various circuits shown here may be included on one or more integrated circuits, may be formed of discrete components, or made be formed of a combination thereof. For example, connection detect circuit 210 and contamination detect 220 may be formed on an integrated circuit that may or may not include host circuitry 230. Calibration resistor RCAL may be a separate and discrete component, or it may be formed on an integrated circuit with contamination detect circuit 220. Active pull-down 260 may be formed on an integrated circuit that may or may not include host circuitry 270, or it may be formed using discrete components.

In various embodiments of the present invention, host device 110 may detect a connection to an accessory. Host device 110 may then determine whether a possibly caustic contaminant is present at a contact. An example is shown in the following figure.

Figure 3:
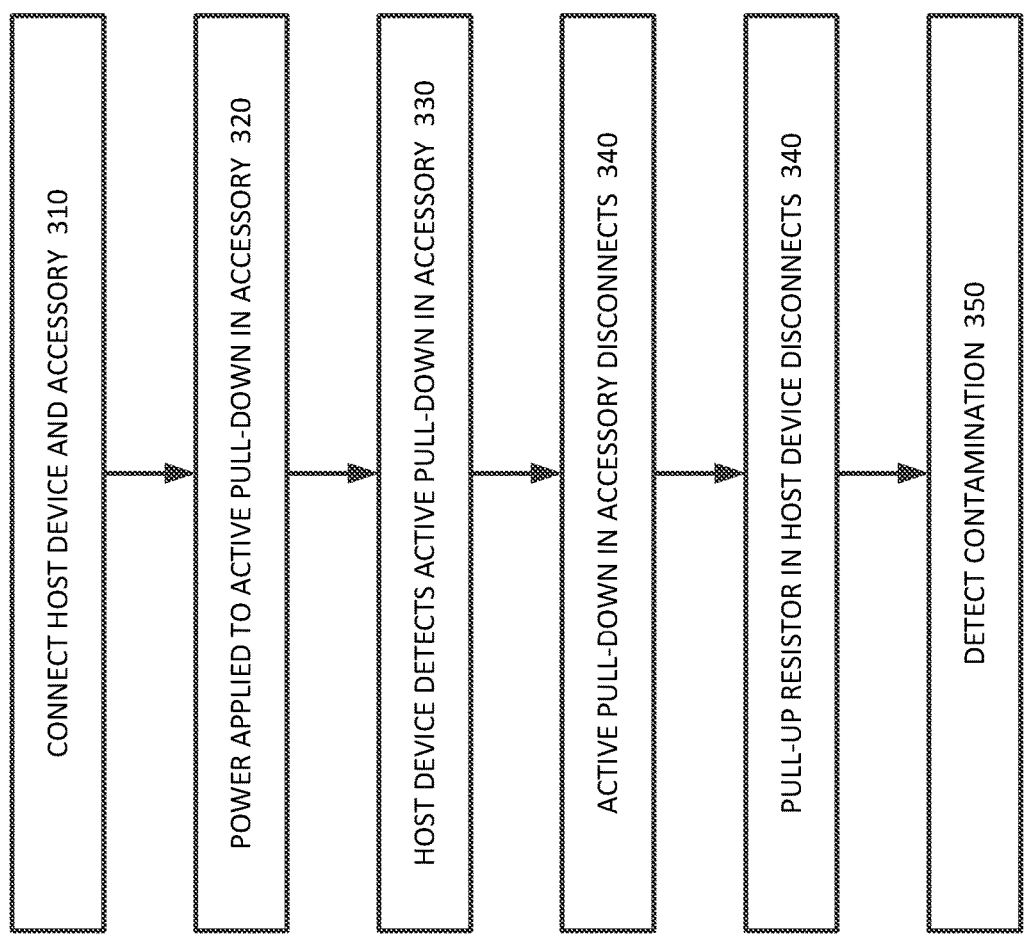
FIG. 3 is a flowchart of the operation of an electronic system according to an embodiment of the present invention.

FIG. 3 is a flowchart of the operation of an electronic system according to an embodiment of the present invention. In this example, a host device and an accessory are connected. Power may be applied to an active pull-down in the accessory in act 320. The host device may detect the active pull-down in the accessory in act 330. Afterwards, in act 340, the active pull-down in the accessory may disconnect, thereby providing a high impedance or open circuit. The presence of contaminations on a contact may be determined in act 350.

In these examples, power may be provided by the host device 110 to accessory 120, or accessory 120 may provide power to host device 110. Accordingly, in act 320, power may be applied to an active pull-down in the accessory either by the accessory itself or the host device.

Again, connection detect circuitry 210 in host device 110 may include a pull-up resistor. When connected to a pull-down resistor in accessory 120, a voltage at device power contact 112 may drop. This drop in voltage may be detected and used to determine that a connection has been made. An example of one such connection detect circuit is shown in the following figure.

Figure 4:
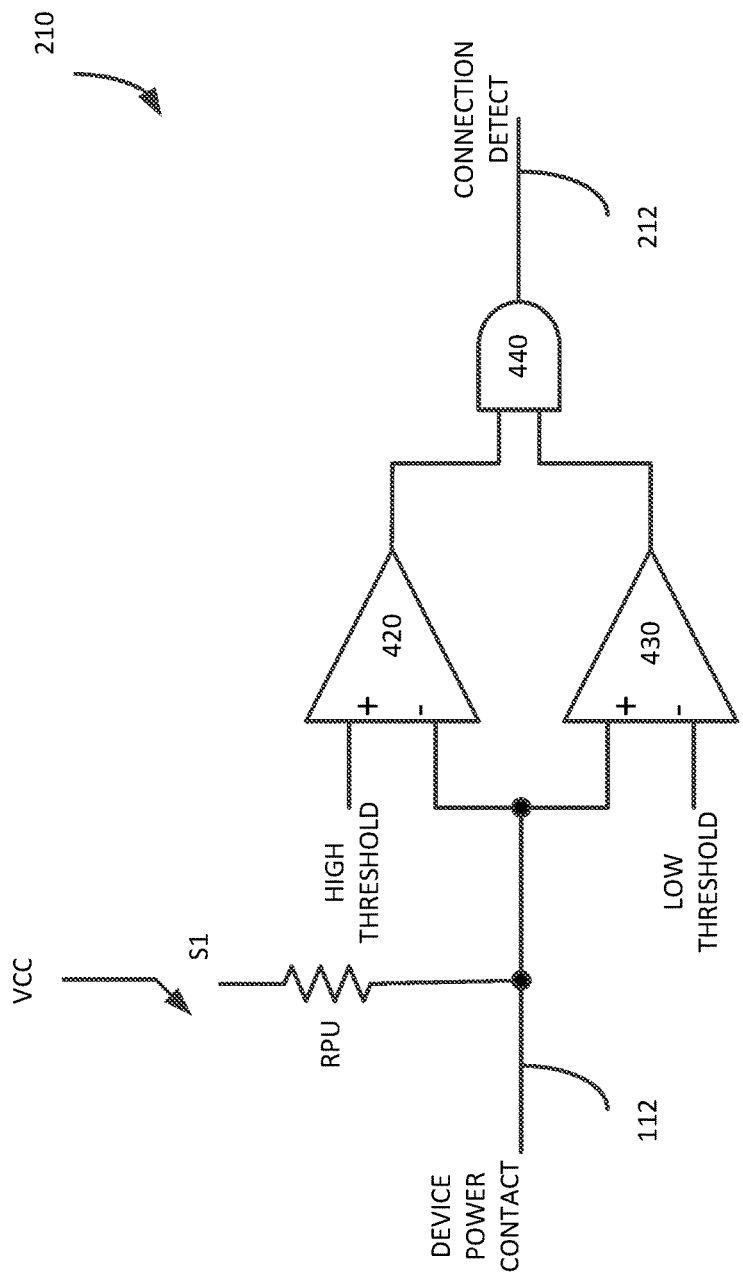
FIG. 4 illustrates an example of a connection detect circuit according to an embodiment of the present invention.

FIG. 4 illustrates an example of a connection detect circuit according to an embodiment of the present invention. Connection detect circuitry 210 may include pull-up resistor RPU, which may be connected between a power supply VCC and device power contact 112. A window comparator may have an input coupled to device power contact 112. When accessory 120 is connected to a host device 110 having this circuit, a pull-down resistor in accessory 120 may connect to device power contact 112. This may pull down the voltage on device power contact 112, lowering the voltage from VCC to an intermediate voltage between VCC and ground. When the voltage on device power contact 112 is between a high threshold voltage and a low threshold voltage, the output of the window comparator on line 212 may go high, thereby indicating that a connection has been detected.

More specifically, a window comparator may include a first comparator 420 that compares a high threshold voltage to a voltage on device power contact 112. The window comparator may include a second comparator 430, which may compare the voltage on device power contact 112 to a low threshold voltage. When a voltage on device power contact 112 is between the high threshold voltage and the low threshold voltage, the outputs of both comparators 420 and 430 may be high. Accordingly, the output of AND gate 440 may similarly go high, thereby indicating the presence of a connection detect on line 212.

Following a connection detect, a host device may determine whether a contaminant is present at device power contact 112. The more current paths that are present at device power contact 112, the more difficult it may be to determine whether such a contaminant is present at device power contact 112. Accordingly, following a connection detect, pull-up resistor RPU may be disconnected from device power contact 112. This disconnection may be made by including a switch in series with the pull-up resistor RPU. In this example, switch S1 may be in series between the pull up resistor RPU and the power supply VCC. As with the other switches and transistors shown here, switch S1 may be a transistor such as a P-channel metal-oxide-semiconductor field-effect transistor (MOSFET), an N-channel MOSFET, bipolar or the type of transistor, microelectronic mechanical (MEM) switch, relay, or other type of switch.

To further reduce current paths that are connected to device power contact 112, a pull-down resistor in accessory 120 may be provided using active pull-down 260. An example of such a circuit is shown in the following figure.

Figure 5:
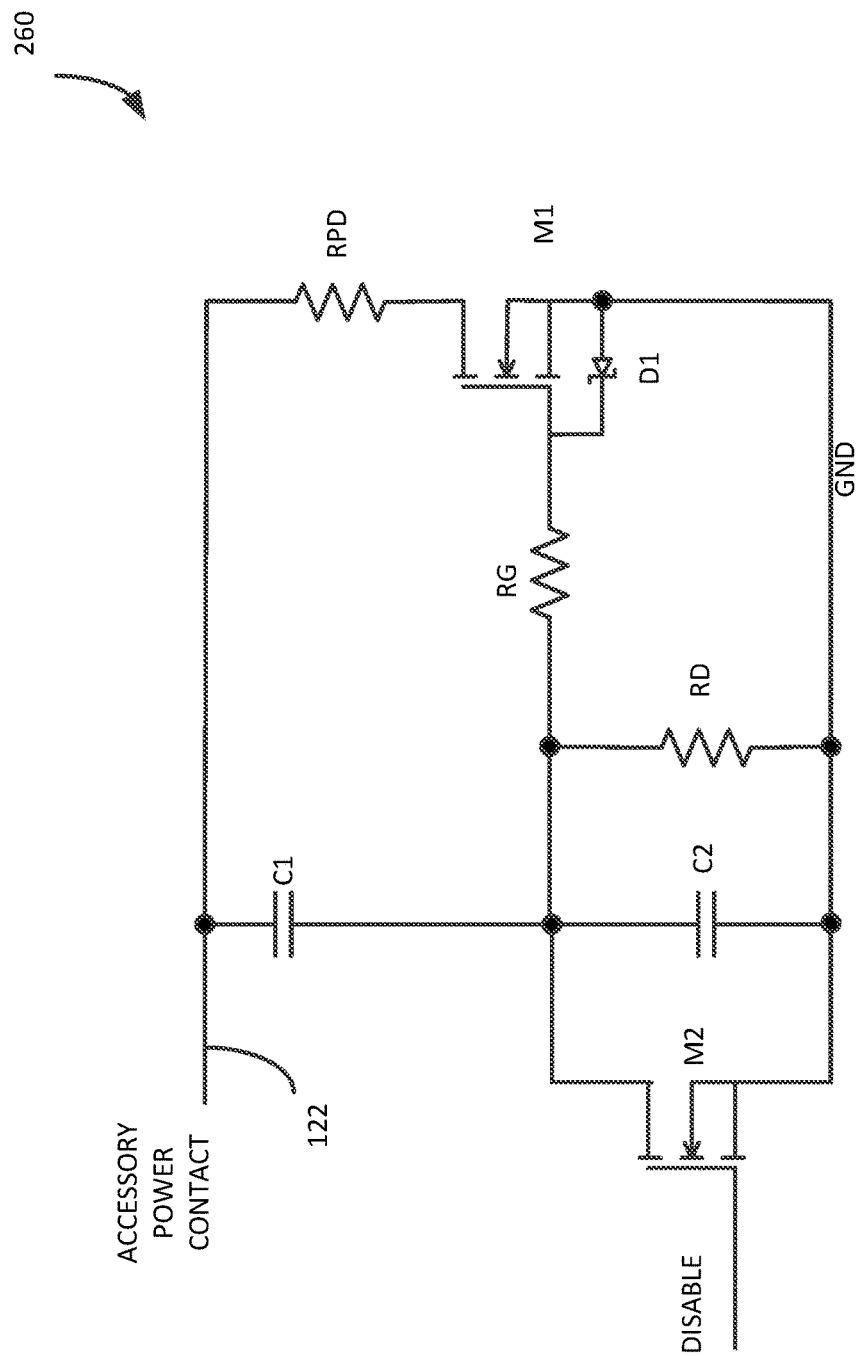
FIG. 5 illustrates an active pull-down according to an embodiment of the present invention.

FIG. 5 illustrates an active pull-down according to an embodiment of the present invention. Active pull-down 260 may receive power from accessory power contact 122. A pull-down resistor RPD may be in series with transistor M1 between the accessory power contact 122 and ground. A capacitor divider including capacitors C1 and C2 may be connected between accessory power contact 122 and ground. A midpoint of the capacitor divider may be coupled to a gate of transistor M1. As power is applied to active pull-down 260 at accessory power contact 122, a voltage at the midpoint of the capacitor divider may increase, thereby turning on transistor M1. The pull-down resistor PRD may be detected by connection detect circuit 210 in host device 110, and host device 110 may determine that a connection to accessory 120 has occurred.

A discharge resistor RD may be connected across capacitor C2 from the midpoint of the capacitor divider to ground. Resistor RPD may bleed charge from capacitor C2 to ground, thereby turning off transistor M1 after the first duration, where the first duration is determined by the initial voltage on C2, the sizes of C2 and RD, and the threshold voltage VT of transistor M1.

If the voltage on accessory power contact 122 were to increase to a high voltage at too fast a rate, transistor M1 could be damaged. Accordingly, active pull-down circuit 260 may include current limiting resistor RG coupled between the midpoint of the capacitors divider and the gate of transistor M1. Also, Zener diode D1 may be connected having a cathode connected to the gate of transistor M1 and an anode connected to a source of transistor M1. The current limiting resistor RG and Zener diode D1 may prevent excessive and possibly damaging voltages from appearing at the gate of transistor M1. Specifically, the gate-to-source voltage of M1 may be limited to a breakdown voltage of the Zener diode (often around 7 Volts.) Active pull-down 260 may be disabled by transistor M2. Specifically, a high-voltage at the gate of transistor M2 may turn off transistor M1, thereby disconnecting the pull-down resistor RPD.

It should be noted that as M1 turns off, the voltage at the accessory power contact 122 may rise due to the disconnection of the pull-down resistor RPD. This may provide an increase in voltage at the midpoint of the capacitor divider, which may cause M1 once again to turn on and conduct. In a worst-case scenario a sustained oscillation may occur. This may be avoided or mitigated by disconnecting the pull-up RPU in connection detect circuit 210 in host device 110 after a connection has been detected. That is, disconnecting RPU may prevent a rise in voltage at the accessory power contact 122 following a connection detect, which may prevent M1 from turning on a second time. Care should be taken to properly time the disconnection of the pull-up resistor RPU, particularly since the connection detect circuit 210 and active pull-down 260 are in separate devices.

Again, after host device 110 detects a connection to accessory 120, host device 110 may detect whether a possibly corrosive contaminant is present at a contact. An example of a circuit that may be used is shown in the following figure.

Figure 6:
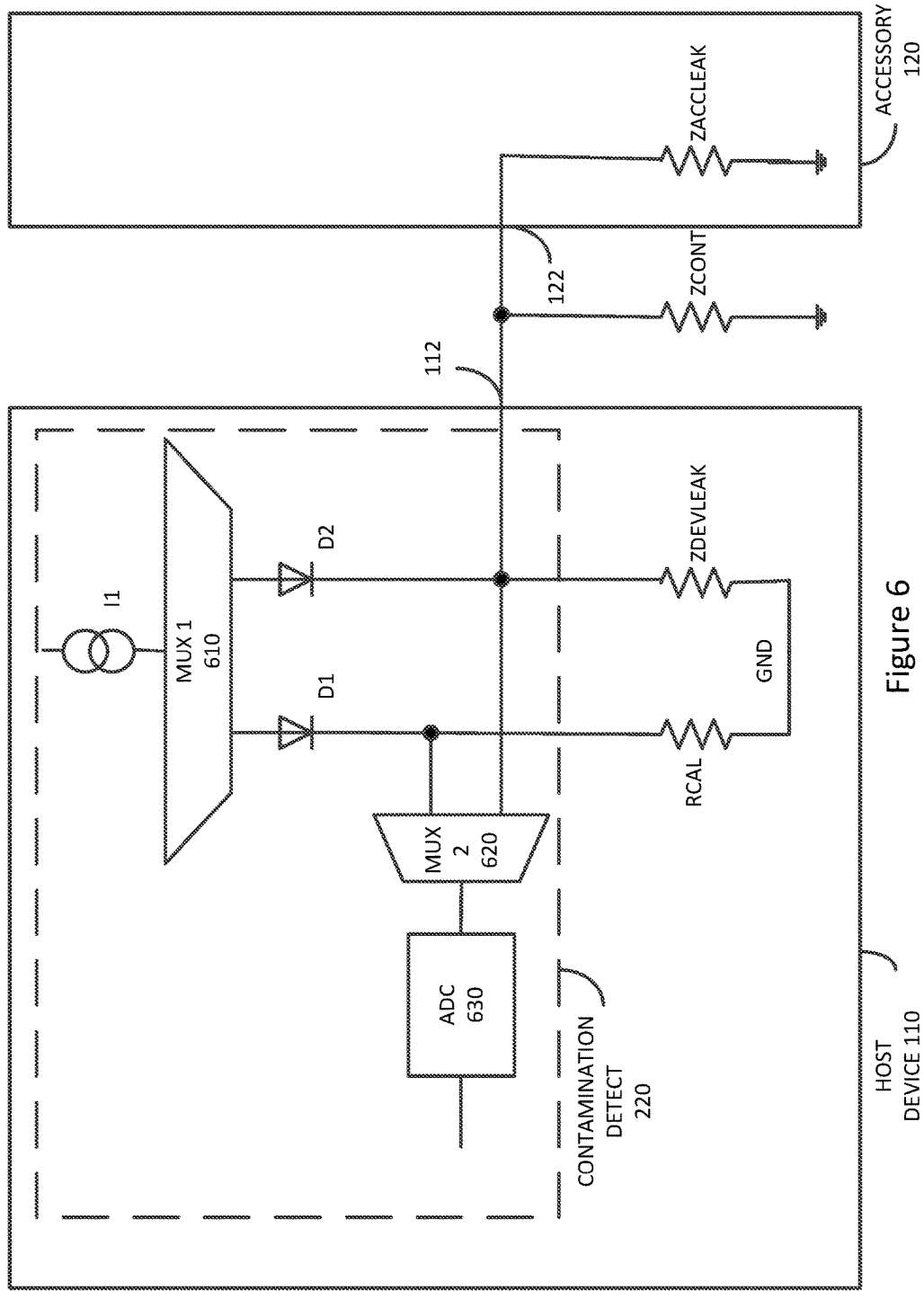
FIG. 6 illustrates a contamination detect circuit according to an embodiment of the present invention.

FIG. 6 illustrates a contamination detect circuit according to an embodiment of the present invention. Contamination detect circuit 220 may provide a current to device power contact 112. Contamination detect circuit 220 may measure a resulting voltage and determine whether a possibly corrosive contaminant is present at device power contact 112. Specifically, if in the impedance at device power contact 112 is sufficiently low, the presence of a contaminant may be inferred.

Specifically, current source I1 may provide a current through multiplexer MUX 1 610 to device power contact 112. This current may flow through the impedance of the contaminant, shown here as ZCONT. Multiplexer MUX 2 620 may connect an input of the analog-to-digital converter 630 to device power contact 112. Analog-to-digital converter 630 may measure the voltage at device power contact 112. A potentially corrosive contaminant may reduce the impedance ZCONT and a lower voltage may be measured by analog-to-digital converter 630. This lower voltage may be inferred to indicate that a contaminant is present at device power contact 112.

Current sources, such as current source I1, have various tolerances associated with them, and even more so when they are included on an integrated circuit. Accordingly, contamination detect circuit 220 may include a calibration loop. Specifically, a current form current source I1 may be selectively provided by multiplexer MUX 1 610 to calibration resistor RCAL. Multiplexer MUX 2 620 may selectively connect calibration resistor RCAL to an input of analog-to-digital converter 630. Analog-to-digital converter 630 may convert this voltage to a digital value that may be used to calibrate measurements made at the device power contact 112.

In these and other embodiments of the present invention, a value of I1 may be determined during a calibration routine by providing I1 to a known resistor, RCAL and measuring the resulting voltage. The measured voltage divided by the value of resistance of RCAL is the value of the current I1. The known current I1 may then be applied to device power contact 112. The resulting voltage may be measured and divided by the value of I1 to determine the impedance at device power contact 112.

There may be various impedances associated with circuitry connected to device power contact 112. For example, there may be stray or leakage paths in host device 110 that are connected to device power contact 112. These impedances and leakage paths may be modeled as the impedance ZDEVLEAK. This impedance may be modeled as impedance from device power contact 112 to ground, though in other circuits it may be modeled as an impedance from device power contact 112 to a power supply, or it may be modeled as other impedances. Similarly, accessory 120 may include leakage paths that may be modeled as an impedance ZACCLEAK.

In various embodiments of the present invention, the impedances ZDEVLEAK and ZACCLEAK may be determined or read from memory and used in calculations to more accurately determine an impedance ZCONT of a contaminant. For example, the host device impedance ZDEVLEAK may be determined during manufacturing and stored in a register on device 110. In other embodiments the present invention, ZDEVLEAK may be determined at various times, for example when an accessory 120 is not connected. Accessory impedance ZACCLEAK may be determined by a manufacturer or other party and stored in a register on accessory 120. This register may be read by host device 110 following a connection of accessory 120. Either or both of these impedances may be recorded as a function of temperature, supply, or other variable.

The net impedance at the device power contact 112 may be equal to the parallel combination of ZDEVLEAK (the impedance of the host device), ZACCLEAK (the impedance of the accessory), and ZCONT (the impedance of the contaminant.) Since the net impedance at device power contact 112 may be measured, and ZDEVLEAK and ZACCLEAK may be determined, ZCONT may be calculated. When ZCONT is below an expected value, the presence of contamination may be inferred. Alternatively, the expected value of the parallel combination of ZDEVLEAK (the impedance of the host device) and ZACCLEAK (the impedance of the accessory) may be determined. If the measured impedance is less than the expected value by more than a threshold or tolerance amount, the presence of contamination may be inferred.

In these and other embodiments of the present invention, host device 110 may determine whether contaminants are present at device power contact 112 when no accessory is present. In this case, the impedance at the device power contact 112 may be equal to the parallel combination of ZDEVLEAK (the impedance of the host device) and ZCONT (the impedance of the contaminant.) When ZCONT is below an expected value, the presence of contamination may be inferred. Alternatively, the expected value of ZDEVLEAK (the impedance of the host device)) may be determined. If the measured impedance is less than the expected value by more than a threshold or tolerance amount, the presence of contamination may be inferred.

In various embodiments of the present invention, the calibration resistor RCAL may be an external precision resistor. For example, RCAL may have a tolerance of 0.1%, 1%, 2%, or other tolerance. This resistor may be a discrete resistor that is not integrated on an integrated circuit that may include contamination detect circuitry 220. In other embodiments of the present invention, the calibration resistor RCAL may be integrated on an integrated circuit also include decontamination detect circuit 220. In such a situation, calibration resistor RCAL may be trimmed or otherwise adjusted for the relatively large manufacturing tolerances found on integrated circuits. Values for RCAL, including values over temperature (and supply) may be stored in a register or elsewhere in host device for use in impedance calculations.

Again, the corrosion of a contact may be greatly exacerbated in the presence of an electric field, for example when a voltage is present on a contact. Accordingly, it may be undesirable to provide a current to a contaminated device power contact 112 for an extended period of time. Also, some fairly benign contaminants, such as DI water, may provide a similar impedance as more corrosive contaminants, such as sweat or pool water, after a current has been provided for extended period of time. This convergence of impedances might not occur after a shorter period of time. Accordingly, the current source I1 may provide pulses of current as opposed to a sustained or DC current. In these and other embodiments of the present invention, multiple pulses having a known amplitude and duration relationship may be provided. Resulting voltage measurements may be taken near the end of the pulses or at other times during the pulses, or both. Examples are shown in the following figure.

Figure 7:
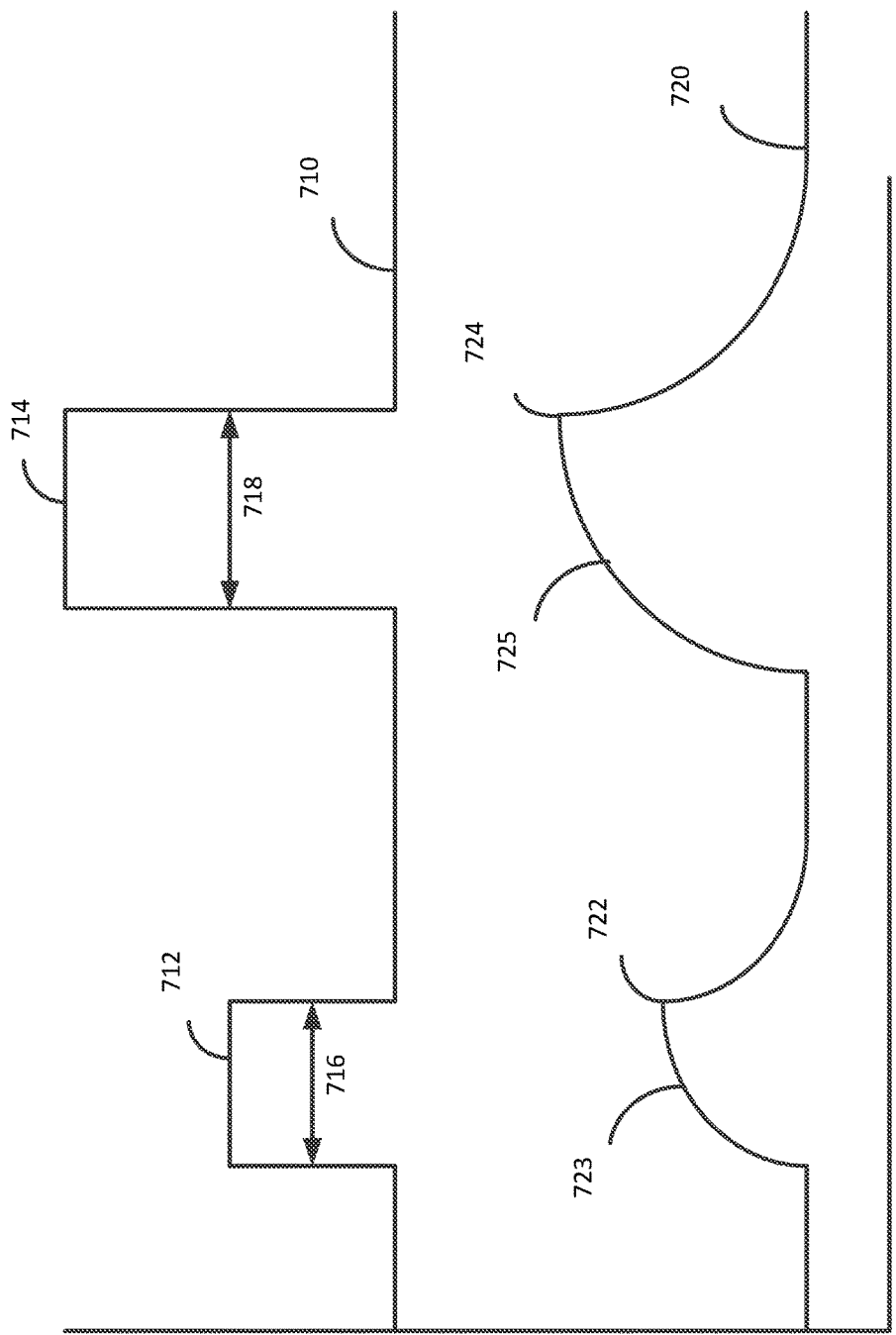
FIG. 7 illustrates current pulses that may be provided to a contamination impedance and a resulting voltage waveform according to an embodiment of the present invention.

FIG. 7 illustrates current pulses that may be provided to a contamination impedance and a resulting voltage waveform according to an embodiment of the present invention. This figure illustrates a waveform 710 including a series of two pulses a first pulse having amplitude 712 duration 716 and a second pulse having amplitude 714 and duration 718. In this example, an amplitude 714 of a first pulse may be twice the amplitude 712 of a second pulse, though the pulses may have an equal amplitude or their amplitudes may be scaled in other ways. The two pulses may have the same duration, or one pulse may have a longer duration than the other. In this example, the second pulse is shown as having a longer duration 718 as compared to the first pulse 716. In other embodiments of the present invention, different numbers of pulses may be used and they may have different amplitude and duration relationships. For example, one, three, four, or more than four pulses may be used. They may have different amplitudes, or two or more pulses may have the same amplitude. They may have different durations, or two or more pulses may have different durations. Waveform 720 illustrates a resulting waveform at a device power contact. Resulting voltages may be measured at various times, for example at times 732 and 724, which are near an end of pulses 712 and 714. In various embodiments of the present invention, one, two, four, six, or more than six voltage measurements or samples may be made using the measurement system of contamination detect circuit 220. In these and other embodiments of the present invention, the amplitude 712 may be equal to 2 microamps, 4 microamps, 8 microamps, 16 microamps, or it may have a different amplitude. The amplitude 714 may be equal to 4 microamps, 8 microamps, 16 microamps, 32 microamps, or it may have a different amplitude. In these and other embodiments of the present invention, the duration 716 may be 50 milliseconds, 100 milliseconds, 200 milliseconds, or it may have a different duration.

When a series of two pulses having different amplitudes are applied to device power contact 112, a measured impedance at the device power contact 112 may be calculated by dividing a difference between the measured resulting voltages by the difference in amplitude of the pulses, $(V1-V2)/(I1-I2)$, where V1 and V2 are the measured resulting voltages and I1-I2 are the amplitudes of the applied current pulses. The measured impedance at the device power contact may again be the parallel combination of ZDEVLEAK (the impedance of the host device), ZACCLEAK (the impedance of the accessory), and ZCONT (the impedance of the contaminant.)

In other embodiments of the present invention, voltages may be measured at other times. For example, voltages may be sampled at pulse midpoints 723 and 725. A slope of the voltage at device power contact 112 may be determined for the last half of the pulses. This derivate of the voltage at the device power contact 112 may then be used to determine whether a contamination is present at device power contact 112.

Figure 8:
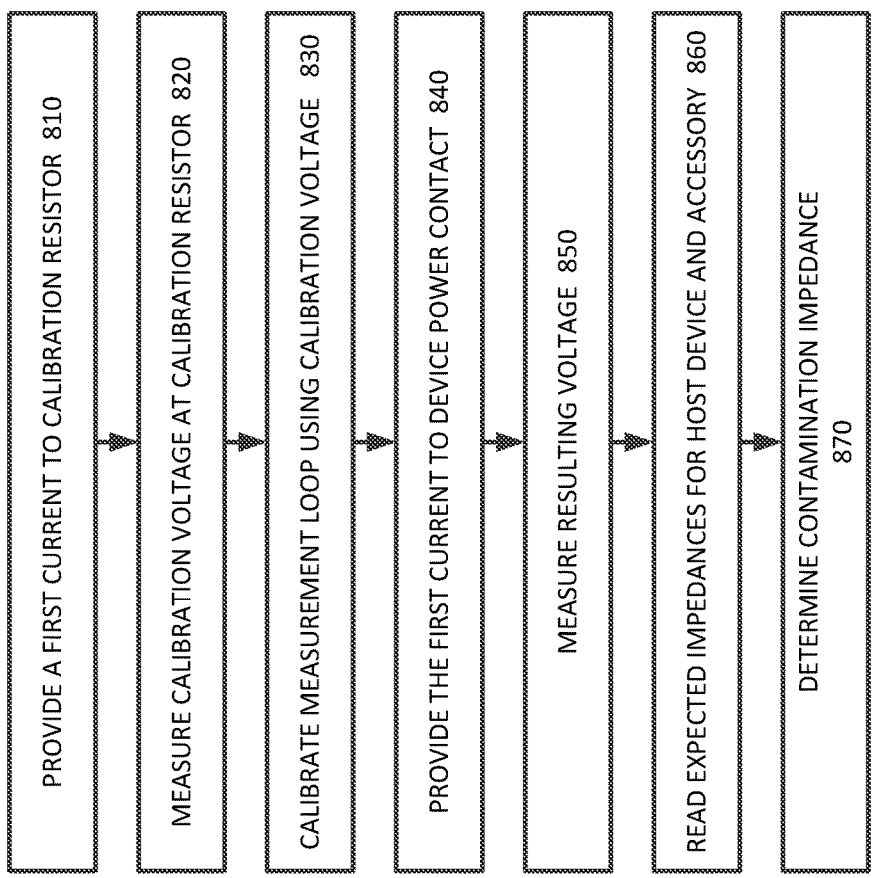
FIG. 8 illustrates the operation of a contamination detect circuit according to an embodiment of the present invention.

FIG. 8 illustrates the operation of a contamination detect circuit according to an embodiment of the present invention. In act 810, a first current may be provided to a calibration resistor. The resulting voltage may be measured in act 820 and used to calibrate the first current in act 830. More specifically, the resulting voltage may be divided by the known value of the calibration resistor to determine the value of the first current. The first current may then be provided to a device power contact in act 840. The resulting voltage may be measured in act 850. The resulting voltage divided by the known first current may be the measured impedance at the device power contact. Expected impedances for the host device and accessory may be read or determined an act 860. In act 870, an impedance of any contamination may be determined using the expected impedances for the host device and accessory and the measured impedance at the device power contact. From this, it may be determined whether a contaminant is present at device power contact 112.

Various actions may be taken when the presence of a contaminant is detected at device power contact 112. For example, host device 110 may reduce the magnitude of, or eliminate, the power being provided at device power contact 112. Also, or instead, an indication or message may appear on a screen of either or both host device 110 and accessory 120 indicating the presence of such contamination to a user. Also, specific guidelines or suggestions for removing the contamination may be included in this message. Other types of indications, for example beeps, flashing lights, vibrations, dots or other shapes having specific colors, or other may be used to indicate the presence of such contamination. These and other messages and indications may also, or instead, be transmitted to a third electronic device, for example a third device that operate in conjunction with the host device 110 and accessory 120.

On occasion, an impedance at device power contact 112 may be high enough to be out of the range of the measurement circuit in contamination detect circuit 220. For example, the impedance at device power contact 112 may be sufficiently high that it results in a voltage that is above the range of analog-to-digital converter 630. In such a case, the impedance at device power contact 112 may be lowered in a controlled way by shorting or connecting the calibration resistor RCAL to device power contact 112.

When RCAL is shorted to device power contact 112, a measured impedance may be the parallel combination of RCAL (the resistance of the calibration resistor), ZDEVLEAK (the impedance of the host device), ZACCLEAK (the impedance of the accessory), and ZCONT (the impedance of the contaminant.) Again, when ZCONT is below a set value, the presence of contamination may be inferred. Alternatively, the expected value of the parallel combination of RCAL (the resistance of the calibration resistor), ZDEVLEAK (the impedance of the host device), and ZACCLEAK (the impedance of the accessory) may be determined. If the measured impedance is less than the expected value by more than a threshold or tolerance amount, the presence of contamination may be inferred. An example of this circuit is shown in the following figure.

Figure 9:
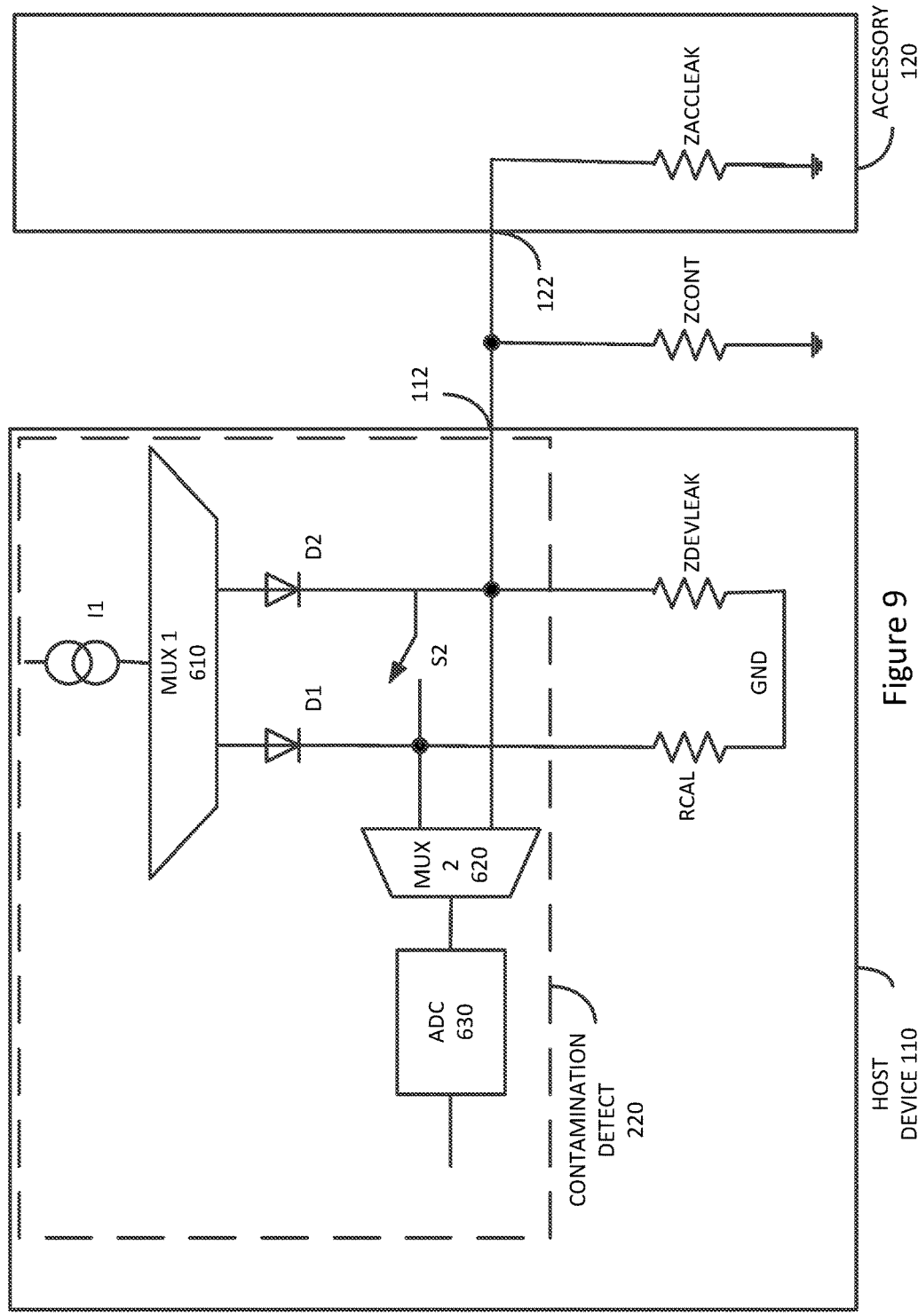
FIG. 9 illustrates another contamination detect circuit according to an embodiment of the present invention.

FIG. 9 illustrates another contamination detect circuit according to an embodiment of the present invention. In this example, switch S2 may be coupled between RCAL and device power contact 112. When ZCONT is high, a resulting voltage may be beyond the range of analog-to-digital converter 630. To extend the range of analog-to-digital converter 630, switch S2 may close, thereby connecting RCAL and device power contact 112. The inclusion of RCAL in the parallel combination of impedances might not impair contamination measurement since RCAL is a known resistance.

In these and other embodiments of the present invention, a value of I1 may be determined during a calibration routine by opening switch S2, providing I1 the known resistor, RCAL, and measuring the resulting voltage. The measured voltage divided by the value of resistance of RCAL is the value of the current I1. The known current I1 may then be applied to device power contact 112 with switch S2 closed. The resulting voltage may be measured and divided by the value of I1 to determine the net impedance at device power contact 112.

The net impedance at the device power contact 112 may be equal to the parallel combination of RCAL (the resistance of the calibration resistor), ZDEVLEAK (the impedance of the host device), ZACCLEAK (the impedance of the accessory), and ZCONT (the impedance of the contaminant.) Since the net impedance at device power contact 112 may be measured, RCAL is known, and ZDEVLEAK and ZACCLEAK may be determined, ZCONT may be calculated. When ZCONT is below an expected value, the presence of contamination may be inferred. Alternatively, the expected value of the parallel combination of RCAL (the resistance of the calibration resistor), ZDEVLEAK (the impedance of the host device), and ZACCLEAK (the impedance of the accessory) may be determined. If the measured impedance is less than the expected value by more than a threshold or tolerance amount, the presence of contamination may be inferred.

In these and other embodiments of the present invention, host device 110 may determine whether contaminants are present at device power contact 112 when no accessory is present. In this case, the impedance at the device power contact 112 may be equal to the parallel combination of RCAL (the resistance of the calibration resistor), ZDEVLEAK (the impedance of the host device), and ZCONT (the impedance of the contaminant.) When ZCONT is below an expected value, the presence of contamination may be inferred. Alternatively, the expected value of the parallel combination of RCAL (the resistance of the calibration resistor) and ZDEVLEAK (the impedance of the host device)) may be determined. If the measured impedance is less than the expected value by more than a threshold or tolerance amount, the presence of contamination may be inferred.

Figure 10:
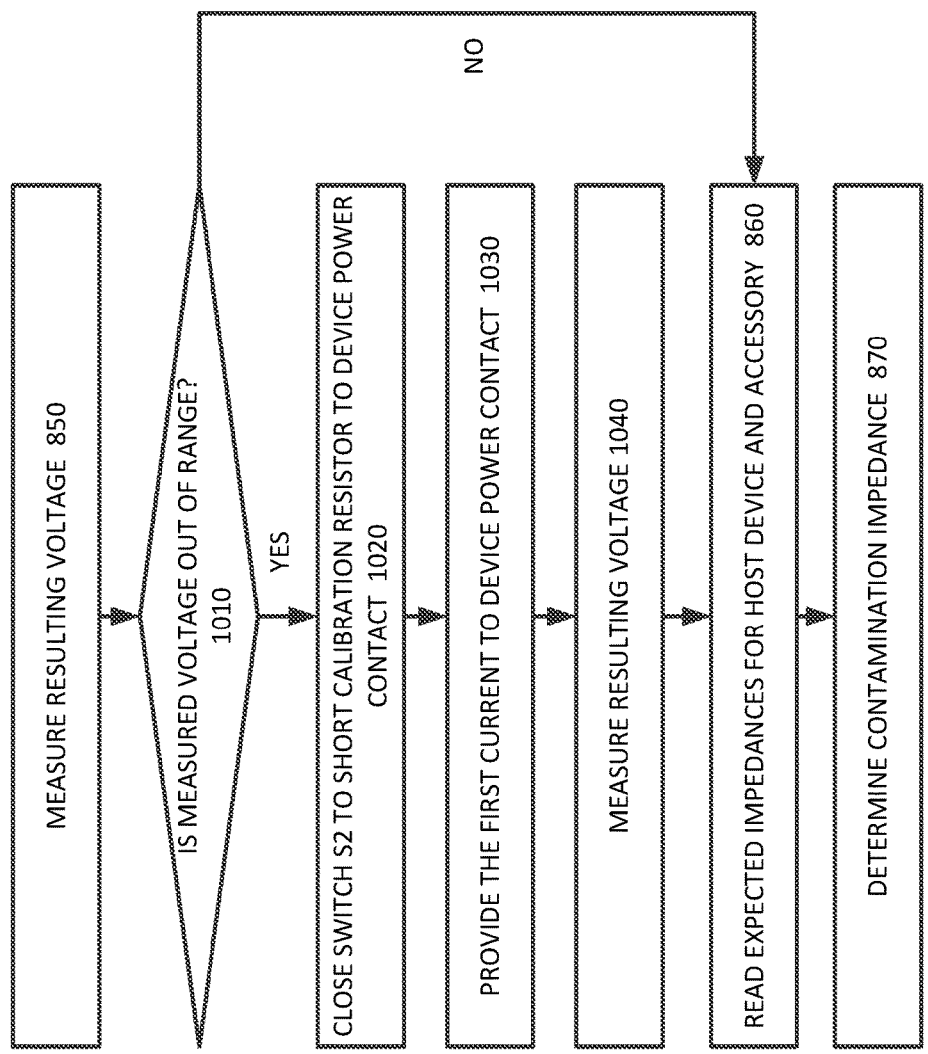
FIG. 10 illustrates a modification to the flowchart of FIG. 8 according to an embodiment of the present invention.

FIG. 10 illustrates a modification to the flowchart of FIG. 8 according to an embodiment of the present invention. As before in FIG. 8, following a calibration routine, a current may be provided to device power contact 112. In act 850, a resulting voltage may be measured. In act 1010, it may be determined whether the measured voltage is out of range of a measurement system. It is not, then as before, expected impedances for the host device and accessory may be read in act 860. In act 870, the contamination impedance may again be determined, and from this, it may be determined whether such contamination is present at the device power contact.

If the measured voltage is out of range in act 1010, switch S2 may be closed, thereby shorting the calibration resistor RCAL to device power contact, in act 1020. A first current may again be applied to the device power contact in act 1030, and the resulting voltage may be measured in act 1040. Once again, in act 860, expected impedances for the host device and accessory may be read or determined, and the contamination impedance may be determined an act 870.

In these and other embodiments of the present invention, various circuits may be used for connection detect circuit 210 and contamination detect circuit 220. An example of another circuit that may be used as contamination detect circuit 220 is shown in the following figure.

Figure 11:
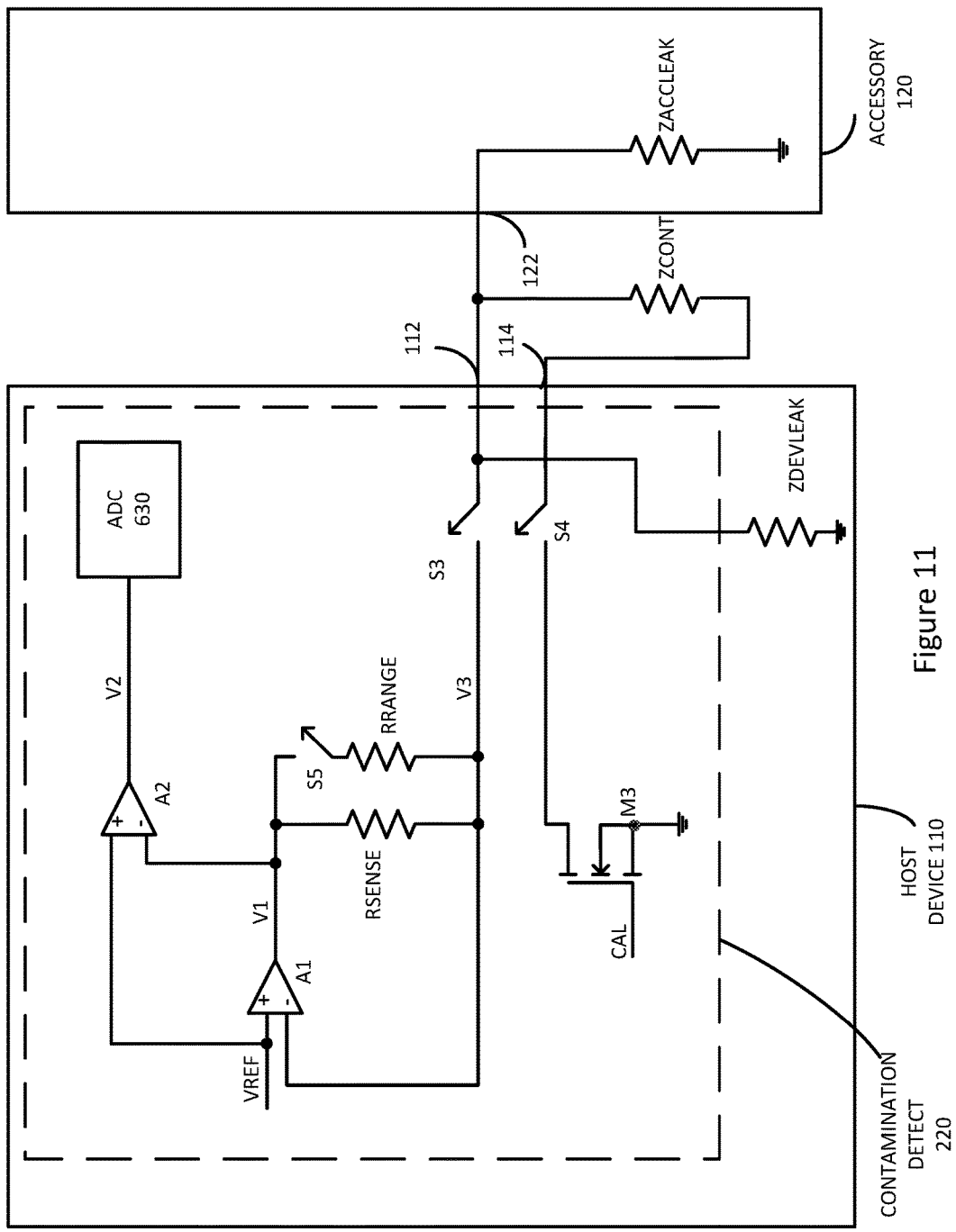
FIG. 11 illustrates another contamination detect circuit according to an embodiment of the present invention.

FIG. 11 illustrates another contamination detect circuit according to an embodiment of the present invention. In this example, a voltage source may be applied between two contacts. A sense circuit may measure a resulting current through the voltage source. When a contaminant is present between the two contacts, the impedance between the contacts may be reduced as compared to when no contaminant is present, and a resulting current may be measured. The resulting current may indicate that contamination is present between the two contacts. As with the other examples shown herein, the contacts may be power supply, ground, bias, enable or other control signal, or other types of contacts.

Specifically, a reference voltage VREF may be received at a noninverting input of amplifier A1. An output of amplifier A1 on line V1 may connect to a sense resistor RSENSE. The other end of the RSENSE resistor may connect to an inverting input of amplifier A1. In this configuration, amplifier A1 may drive its output on line V1 to a voltage that is needed to keep the voltage on line V3 at or near the reference voltage VREF. The voltage on line V3 may be connected to contact 112 and ground may be connected to contact 114. In this way, a voltage source equal to the reference voltage VREF may be connected across contacts 112 and 114.

When a contamination detect sequence is performed, switch S3 may close thereby connecting contact 112 to line V3. Switch S4 may close connecting contact 114 to a drain of transistor M3.

When no contamination is present between contacts 112 and 114, the contamination impedance ZCONT may be high and there may be an open circuit between them. No or minor current may flow through the sense resistor RSENSE. A reference voltage VREF may be received at a noninverting input of amplifier A1 and the amplifier may drive its output voltage on line V1 such that a voltage on line V3 received at its inverting input may be at least approximately equal to the reference voltage VREF. With ZCONT high, the voltage drop across the sense resistor RSENSE may be minimal. Accordingly, the voltage on line V1 may also be at or near the reference voltage VREF. Since the voltage on line V3 is held to VREF by amplifier A1, instrumentation amplifier A2 may receive a signal that is equal to a signal across the sense resistor RSENSE. Instrumentation amplifier A2 may amplify this signal and provide an output on line V2 to analog-to-digital converter 630.

When contamination is present between contacts 112 and 114, the contamination impedance ZCONT may be reduced. In this case, current may flow through the voltage source provided across contacts 112 and 114. The result is that current may flow through the sense resistor RSENSE. As this current flows, a voltage on line V3 may be pulled lower. Again, line V3 is connected to an inverting input of amplifier A1, while the noninverting input of amplifier A1 is connected to receive a reference voltage VREF. Accordingly, amplifier A1 may drive the voltage V1 at the output of amplifier A1 higher, such that the voltage on line V3 remains at or near the voltage VREF. That is, the voltage on line V3 may be maintained to be at least approximately the VREF. The instrumentation amplifier A2 may receive the voltage across the sense resistor RSENSE as an input. Instrumentation amplifier A2 may amplify this signal and provided an output on line V2 to analog-to-digital converter 630.

Low values for contamination impedance ZCONT may generate large currents in sense resistor RSENSE. This may generate voltages beyond a range of amplifier A1, instrumentation amplifier A2, or analog-to-digital converter 630. Accordingly, resistor RRANGE may be used to extend a range of contamination detect circuit 220. Specifically, switch S5 may be close, connecting resistor RRANGE in parallel with resistor RSENSE. This reduced sense impedance may lower a voltage across RSENSE such that it may be processed by amplifier A1, instrumentation amplifier A2, and analog-to-digital converter 630.

In this example, transistor M3 may be a current limiting transistor that may limit current when contacts 112 and 114 are shorted together during a contamination detect sequence. As before, device impedance ZDEVLEAK and accessory impedance ZACCLEAK are shown as being connected to contact 112. Similar impedances may be shown as being connected to contact 114 but are omitted for clarity. Also, the impedances connected to contact 114 may generate a minimal current flow since contact 114 maybe grounded during a contamination detect routine. It may also be noted that applying a constant voltage to the device contacts may eliminate a voltage dependency component of the values of ZCONT, ZDEVLEAK, and ZACCLEAK. As before, value for ZDEVLEAK, and ZACCLEAK may be read from registers or otherwise determined and used in calculating ZCONT and determining whether a contaminant exists between contacts 112 and 114.

Figure 12:
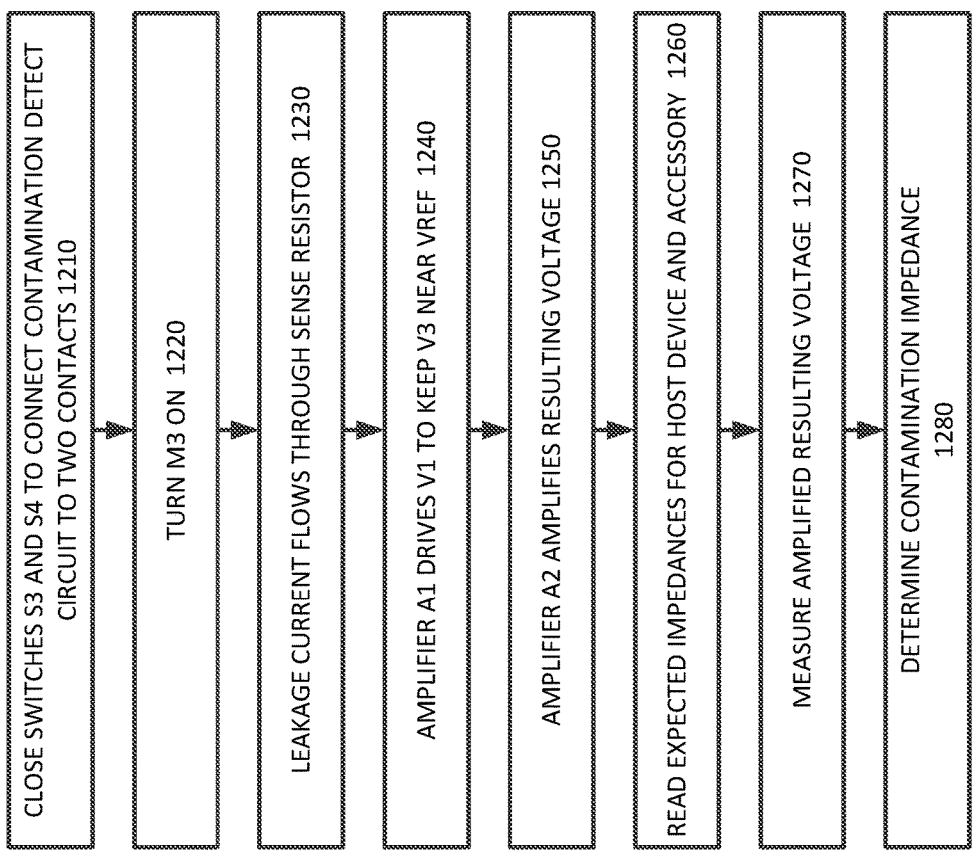
FIG. 12 illustrates the operation of a contamination detect circuit according to an embodiment of the present invention.

In these and other embodiments of the present invention, the voltage source may provide a voltage that is at least approximately equal to the reference voltage VREF. This reference voltage may be a low voltage of approximately 0.5 volts or less. The device impedance and accessory impedance may be increased at this low voltage level and may therefore have less of an impact. Also, when there is contamination present between contact 112 and 114, the contamination detect routine may cause a reduced amount of corrosion as compared to a higher voltage for VREF, or compared to voltages generated during measurements performed by the constant current impedance measurement embodiment as described previously here FIG. 12 illustrates the operation of a contamination detect circuit according to an embodiment of the present invention. In act 1210, switches S3 and S4 may close, connecting contamination detect circuit across two contacts 112 and 114 of a host device 110. In act 1220, transistor M3 may turn on. This, along with the closing of the switches S3 and S4, may connect a voltage source across the two contacts 112 and 114. Leakage current, if present, may flow through the sense resistor RSENSE in act 1230. Amplifier A1 may drive its output voltage V1 to a voltage needed to keep a voltage on line V3 near the voltage reference VREF in act 1240. The instrumentation amplifier A2 may amplify a resulting voltage across the sense resistor in act 1250. In act 1260, expected impedances for the host and device and accessory may be read. The amplified resulting voltage may be measured in act 1270, and from the expected values and this measurement, the contamination impedance ZCONT may be calculated in act 1280. From the calculated impedance, the presence of contamination may be determined, as before.

In these examples, a connection detect circuit and contamination detect circuit may be located on a host device, while an active pull-down may be located on an accessory. In these and other embodiments of the present invention, a connection detect circuit and contamination detect circuit may be located on an accessory, while an active pull-down may be located on a host device.

Also, in these examples, the connection detect circuit and the contamination detect circuit may be connected to the same contact. In these and other embodiments of the present invention, the connection detect circuit and the contamination detect circuit may be connected to separate and different contacts. Also, in these examples, the connection detect circuit and the contamination detect circuit may be connected to a power contact.

In these and other embodiments of the present invention, the connection detect circuit and the contamination detect circuit may be connected to a contact other than a power contact. For example, either or both the connection detect circuit and the contamination detect circuit may be connected to another type of contact such as a contact used for an enable signal, low-frequency data signal, or other data, control, bias, supply, or other type of contact.

Embodiments of the present invention may provide contacts for connector receptacles and connector inserts that may be located in, and may connect to, various types of devices, such as portable computing devices, tablet computers, desktop computers, laptops, all-in-one computers, wearable computing devices, cell phones, smart phones, media phones, storage devices, portable media players, navigation systems, monitors, power supplies, video delivery systems, adapters, remote control devices, chargers, and other devices. These contacts may provide pathways for power and signals that are compliant with various standards such as one of the Universal Serial Bus (USB) standards including USB Type-C, High-Definition Multimedia Interface (HDMI), Digital Visual Interface (DVI), Ethernet, DisplayPort, Thunderbolt, Lightning, Joint Test Action Group (JTAG), test-access-port (TAP), Directed Automated Random Testing (DART), universal asynchronous receiver/transmitters (UARTs), clock signals, power signals, and other types of standard, non-standard, and proprietary interfaces and combinations thereof that have been developed, are being developed, or will be developed in the future. Other embodiments of the present invention may provide contacts that may be used to provide a reduced set of functions for one or more of these standards. In various embodiments of the present invention, these contacts may be used to convey power, ground, signals, test points, and other voltage, current, data, or other information.

The above description of embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated. Thus, it will be appreciated that the invention is intended to cover all modifications and equivalents within the scope of the following claims.

What is claimed is:

1. An electronic system comprising:
    a host device comprising:
        host circuitry to execute functions of the host device;
        a device contact coupled to the host circuitry, the device contact to form an electrical connection with a corresponding accessory contact of an accessory when the host device is mated with the accessory;
        a connection detect circuit coupled to the device contact to detect a connection to the device contact by the corresponding accessory contact, wherein the connection detect circuit detects the connection to the device contact by the corresponding accessory contact during a first duration; and
        a contamination detect circuit coupled to the device contact to detect contamination at the device contact, wherein the contamination detect circuit detects contamination at the device contact after the first duration,
    wherein the connection detect circuit comprises a pull-up resistor having a first terminal coupled to the device contact, the first terminal of the pull-up resistor further coupled to an input of a window comparator.

2. The electronic system of claim 1 wherein the contamination detect circuit comprises:
    a calibration circuit comprising:
        a calibration resistor;
        a current source circuit coupled to a first terminal of the calibration resistor to provide a first current through the calibration resistor; and
        a measurement circuit to measure a resulting calibration voltage at the first terminal of the calibration resistor; and
    a voltage measuring circuit comprising:
        the current source circuit to provide a second current to the device contact; and
        the measurement circuit to measure a resulting contamination voltage at the device contact.

3. The electronic system of claim 2 wherein the second current comprises a series of pulses including a first current pulse having a first amplitude for a second duration and a second current pulse having a second amplitude for a third duration.

4. The electronic system of claim 2 wherein the contamination detect circuit further comprises:
    a switch coupled between the first terminal of the calibration resistor and the device contact.

5. The electronic system of claim 4 wherein the measurement circuit comprises:
    a multiplexer having a first input coupled to the first terminal of the calibration resistor and a second input coupled to the device contact; and
    an analog-to-digital converter having an input coupled to an output of the multiplexer.

6. The electronic system of claim 5 wherein the current source circuit is selectively coupled to the first terminal of the calibration resistor and the device contact.

7. The electronic system of claim 6 wherein the contamination detect circuit further comprises a switch coupled between the first terminal of the calibration resistor and the device contact and the switch is closed when the input to the analog-to-digital converter reaches or exceeds a maximum value.

8. An electronic system comprising:
    a host device comprising:
        host circuitry to execute functions of the host device;
        a device contact coupled to the host circuitry, the device contact to form an electrical connection with a corresponding accessory contact of an accessory when the host device is mated with the accessory;
        a connection detect circuit coupled to the device contact to detect a connection to the device contact by the corresponding accessory contact, wherein the connection detect circuit detects the connection to the device contact by the corresponding accessory contact during a first duration; and a contamination detect circuit coupled to the device contact to detect contamination at the device contact, wherein the contamination detect circuit detects contamination at the device contact after the first duration; and the accessory comprising:

the accessory contact to mate with the device contact of the host device; and an active pull-down to provide a pull-down resistance for a second duration following a connection to the host device, and then to provide a high impedance.

9. The electronic system of claim 8 wherein the active pull-down comprises a resistor in series with a transistor.

10. The electronic system of claim 9 wherein the active pull-down further comprises a capacitance divider having a first and second capacitor coupled to a gate of the transistor.

11. The electronic system of claim 10 wherein the active pull-down further comprises:

a resistor in series between the first and second capacitor and the gate of the transistor; and a Zener diode having a cathode coupled to a gate of the transistor and an anode coupled to a source of the transistor.

12. The electronic system of claim 11 wherein the active pull-down further comprises a resistor in series with the second capacitor to discharge the second capacitor and set a length of the second duration.

13. An electronic system comprising:

a host device comprising:

host circuitry to execute functions of the host device;

a device contact coupled to the host circuitry, the device contact to form an electrical connection with a corresponding accessory contact of an accessory when the host device is mated with the accessory;

a connection detect circuit coupled to the device contact to detect a connection to the device contact by the corresponding accessory contact; and a contamination detect circuit coupled to the device contact to detect contamination at the device contact, the contamination detect circuit comprising:

a calibration circuit comprising:

a calibration resistor;

a current source circuit coupled to a first terminal of the calibration resistor to provide a first current through the calibration resistor; and a measurement circuit to measure a resulting calibration voltage at the first terminal of the calibration resistor; and a voltage measuring circuit comprising:

the current source circuit to provide a second current to the device contact; and the measurement circuit to measure a resulting contamination voltage at the device contact.

14. The electronic system of claim 13 further comprising:

the accessory comprising:

the accessory contact; and an active pull-down coupled to the accessory contact to provide a pull-down resistance for a first duration following a connection to the host device and then to provide a high impedance.

15. The electronic system of claim 13 wherein the contamination detect circuit further comprises a switch coupled between the first terminal of the calibration resistor and the device contact.

16. The electronic system of claim 13 wherein the measurement circuit comprises:

a multiplexer having a first input coupled to the first terminal of the calibration resistor and a second input coupled to the device contact; and an analog-to-digital converter having an input coupled to an output of the multiplexer.

17. The electronic system of claim 16 wherein the contamination detect circuit further comprises a switch coupled between the first terminal of the calibration resistor and the device contact and the switch is closed when the input to the analog-to-digital converter reaches or exceeds a maximum value.

18. The electronic system of claim 13 further comprising:

the accessory comprising:

the accessory contact for mating with the device contact of the host device; and an active pull-down coupled to the accessory contact to provide a pull-down resistance for a second duration following a connection to the host device, and then to provide a high impedance, wherein the active pull-down comprises:

a resistor in series with a transistor;

a capacitance divider having a first and second capacitor coupled to a gate of the transistor.

19. The electronic system of claim 18 wherein the active pull-down further comprises:

a resistor in series between the first and second capacitor and the gate of the transistor;

a Zener diode having a cathode coupled to a gate of the transistor and an anode coupled to a source of the transistor; and a resistor in series with the second capacitor to discharge the second capacitor and set a length of the second duration.

20. The electronic system of claim 13 where the first current and the second current are different currents.

21. The electronic system of claim 13 wherein the second current comprises a series of pulses including a first current pulse having a first amplitude for a third duration and a second current pulse having a second amplitude for a fourth duration.

* * * * *